US009408900B2

(12) United States Patent
Garg et al.

(10) Patent No.: US 9,408,900 B2
(45) Date of Patent: Aug. 9, 2016

(54) **RECOMBINANT VACCINE AGAINST *CLOSTRIDIUM PERFRINGENS* INFECTION AND EPSILON TOXIN INTOXICATION**

(75) Inventors: Lalit Chander Garg, New Delhi (IN); Keshav Gopal, New Delhi (IN); Aparna Dixit, New Delhi (IN)

(73) Assignee: National Institute of Immunology, New Delhi (IN)

( * ) Notice: Subject to any disclaimer, the term of this patent is extended or adjusted under 35 U.S.C. 154(b) by 505 days.

(21) Appl. No.: 13/808,141

(22) PCT Filed: Jul. 1, 2011

(86) PCT No.: PCT/IB2011/001544
§ 371 (c)(1),
(2), (4) Date: Mar. 18, 2013

(87) PCT Pub. No.: WO2012/004645
PCT Pub. Date: Jan. 12, 2012

(65) Prior Publication Data
US 2013/0183344 A1     Jul. 18, 2013

(30) Foreign Application Priority Data
Jul. 5, 2010   (IN) .......................... 1577/DEL/2010

(51) Int. Cl.
*A61K 39/08* (2006.01)
*C07K 14/33* (2006.01)
*A61K 39/00* (2006.01)

(52) U.S. Cl.
CPC .................. *A61K 39/08* (2013.01); *C07K 14/33* (2013.01); *A61K 2039/55566* (2013.01)

(58) Field of Classification Search
None
See application file for complete search history.

(56) References Cited

U.S. PATENT DOCUMENTS 6,403,094 B1 *   6/2002   Titball et al. ............... 424/190.1

FOREIGN PATENT DOCUMENTS

WO     WO 97/34001     *    9/1997

OTHER PUBLICATIONS

Epsilon toxin, partial Clostridium Perfringens D, GenBank Accession ADF42572 Apr. 21, 2010.*

* cited by examiner

*Primary Examiner* — Oluwatosin Ogunbiyi
(74) *Attorney, Agent, or Firm* — Ladas & Parry LLP

(57) ABSTRACT

The present invention relates to generation and high level expression of recombinant non-toxic of epsilon toxin of *Clostridium perfringens* as a recombinant vaccine against *Clostridium perfringens* infection and a process for producing the vaccine involving amplifying, cloning, transforming, incubating and purifying the recombinant non-toxic epsilon toxin protein. Thus in this invention, substitution mutation Y71G was executed in recombinant Etx and the recombinant EtxY71G protein was over-expressed in soluble form. Expressed protein was purified near homogeneity by DEAE sepharose anion exchange chromatography with high yield. Potential of rEtxY71G as a vaccine candidate was evaluated and found to be highly specific and immunogenic. The present invention is the first report for high level expression of non toxic rEtxY71G mutant protein of *Clostridium perfringens*. Upto 100 mg/L of highly immunogenic and homogeneous recombinant EtxY71G protein of 31 kDa was produced. Further, the immunization with rEtxY71G gave very high titer and conferred protection against epsilon toxin intoxication.

12 Claims, 11 Drawing Sheets

SEQUENCE LISTING

```
<160> NUMBER OF SEQ ID NOS: 3

<210> SEQ ID NO 1
<211> LENGTH: 45
<212> TYPE: DNA
<213> ORGANISM: ARTIFICIAL SEQUENCE
<220> FEATURE:
<223> OTHER INFORMATION: Primer

<400> SEQUENCE: 1
ccatcaatga attatcttga agatgttggt gttggaaaag ctctc            45

<210> SEQ ID NO 2
<211> LENGTH: 45
<212> TYPE: DNA
<213> ORGANISM: ARTIFICIAL SEQUENCE
<220> FEATURE:
<223> OTHER INFORMATION: Primer

<400> SEQUENCE: 2
gagagctttt ccaacaccaa catcttcaag ataattcatt gatgg            45

<210> SEQ ID NO 3
<211> LENGTH: 283
<212> TYPE: PRT
<213> ORGANISM: ARTIFICIAL SEQUENCE
<220> FEATURE:
<223> OTHER INFORMATION: Modified Etx Protein - EtxY71G

<400> SEQUENCE: 3

Met Ala Ser Tyr Asp Asn Val Asp Thr Leu Ile Glu Lys Gly Arg Tyr
1               5                   10                  15
```

-continued

```
Asn Thr Lys Tyr Asn Tyr Leu Lys Arg Met Glu Lys Tyr Tyr Pro Asn
            20                  25                  30

Ala Met Ala Tyr Phe Asp Lys Val Thr Ile Asn Pro Gln Gly Asn Asp
        35                  40                  45

Phe Tyr Ile Asn Asn Pro Lys Val Glu Leu Asp Gly Glu Pro Ser Met
    50                  55                  60

Asn Tyr Leu Glu Asp Val Gly Val Gly Lys Ala Leu Leu Thr Asn Asp
65                      70                  75                  80

Thr Gln Gln Glu Gln Lys Leu Lys Ser Gln Ser Phe Thr Cys Lys Asn
                85                  90                  95

Thr Asp Thr Val Thr Ala Thr Thr Thr His Thr Val Gly Thr Ser Ile
            100                 105                 110

Gln Ala Thr Ala Lys Phe Thr Val Pro Phe Asn Glu Thr Gly Val Ser
            115                 120                 125

Leu Thr Thr Ser Tyr Ser Phe Ala Asn Thr Asn Thr Asn Thr Asn Ser
    130                 135                 140

Lys Glu Ile Thr His Asn Val Pro Ser Gln Asp Ile Leu Val Pro Ala
145                 150                 155                 160

Asn Thr Thr Val Glu Val Ile Ala Tyr Leu Lys Lys Val Asn Val Lys
                165                 170                 175

Gly Asn Val Lys Leu Val Gly Gln Val Ser Gly Ser Glu Trp Gly Glu
                180                 185                 190

Ile Pro Ser Tyr Leu Ala Phe Pro Arg Asp Gly Tyr Lys Phe Ser Leu
        195                 200                 205

Ser Asp Thr Val Asn Lys Ser Asp Leu Asn Glu Asp Gly Thr Ile Asn
    210                 215                 220

Ile Asn Gly Lys Gly Asn Tyr Ser Ala Val Met Gly Asp Glu Leu Ile
225                 230                 235                 240

Val Lys Val Arg Asn Leu Asn Thr Asn Asn Val Gln Glu Tyr Val Ile
                245                 250                 255

Pro Val Asp Lys Lys Glu Lys Ser Asn Asp Ser Asn Ile Val Lys Tyr
            260                 265                 270

Trp Ser Leu Ser Ile Lys Ala Pro Gly Ile Lys
        275                 280
```

RECOMBINANT VACCINE AGAINST *CLOSTRIDIUM PERFRINGENS* INFECTION AND EPSILON TOXIN INTOXICATION

RELATED APPLICATION INFORMATION

This application is a 371 of International Application PCT/IB2011/001544 filed 1 Jul. 2011 entitled "A Recombinant Vaccine Against Clostridium Perfringens Infection And Epsilon (ε) Toxin Intoxication" which was published in the English language on 12 Jan. 2012, with International Publication Number WO 2012/004645 A1, and which claims priority from Indian Patent Application No.: 1577/DEL/2010 filed 5 Jul. 2010, the contents of which are incorporated herein by reference.

FIELD OF INVENTION

The present invention relates to generation and high level expression of non-toxic recombinant EtxY71G protein of *Clostridium perfringens* using prokaryotic expression vector. In particular, the present invention relates to a process for the preparation of the non-toxic recombinant EtxY71G protein. The present invention also relates to the immunogenic potential of the non-toxic recombinant EtxY71G protein and its vaccine potential for the treatment of *Clostridium perfringens* infection and epsilon (ε) toxin intoxication in mice.

BACKGROUND OF THE INVENTION

The genus *Clostridium* consists of a diverse group of Gram-positive, anaerobic and heat resistant spore forming bacteria. They are widely distributed in soil, sewage and water. In addition, some species are normal inhabitant of gastrointestinal tract of mammals. Usually bacterial numbers remain small in intestine but due to some abrupt changes in diet or other factors, bacterial number increases upto $10^9$ cells per gram of ileum contents and secretes large amounts of toxin (Payne and Oyston, 1997). They cause severe diseases in animals and human such as botulism, tetanus, gas gangrene and enterotoxemia. One of the members of this genus, *Clostridium perfringens* causes wide variety of diseases in human such as gas gangrene, food poisoning and necrotic enteritis. The bacterium also causes some severe gastrointestinal and enterotoxemia diseases in domestic animals (Frank, 1956; Songer, 1997a).

The etiology of diseases caused by *Clostridium perfringens* suggests mainly to the production of various extracellular toxins. The bacteria have been divided into five distinct types, A through E, on the basis of production of four major toxins (alpha, beta, epsilon and iota). Epsilon toxin is secreted by type B and D strains (Brooks et al., 1957). *Clostridium perfringens* type B is associated particularly with dysentery in lambs, while type D is associated with necrotic enteritis and enterotoxemia in sheep and lambs, along with a condition known as pulpy kidney or overeating disease (Bullen, 1970). These diseases are usually fatal and are characterized by a short period of time between the first appearance of symptoms and death. The mortality rate can be as high as 100%, and the diseases are of major economic significance, particularly in the area where animals is used for the economic purposes (Buxton and Fraser, 1977). The symptoms of disease, including neurological dysfunction and pulmonary edema, generally appear within an hour of the administration of purified epsilon toxin (Uzal and Kelly, 1997; Uzal and Kelly, 1998) whereas peritoneal and pericardial effusions are common in naturally infected sheep (Jubb et al., 1993). Many animals die per acutely, without premonitory signs (Niilo, 1993; Popoff, 1984). The epsilon toxin can cross the blood-brain barrier (Jover et al., 2007; Worthington and Mulders, 1975) and accumulates in the brain as well as in the kidney, causing widespread osmotic alterations by disrupting vascular endothelia.

Due to their devastating effect, epsilon toxin has been considered as the second most potent toxin after botulinum and titanus (McClane et al., 2005). This toxin has also been included in the Centers for Disease Control list of selected agents that might be used as biological weapons (Atlas, 1998). Epsilon toxin is secreted as an inactive prototoxin of 311 amino acids length (McDonel, 1986), which got activated to a lethal toxin by proteolytic cleavage (Bhown and Habeeb, 1977). The proteases for activation of epsilon toxin are provided by either host or the bacterium, such as trypsin and chymotrypsin by host (Bhown and Habeeb, 1977; Hunter et al., 1992) and lambda protease by bacterium (Jin et al., 1996; Minami et al., 1997). Maximum lethality with an $LD_{50}$ 70 ng/kg occurs when cleavage is done by trypsin and chymotrypsin combination, resulting in the loss of 13 N-terminal residues and 29 C-terminal residues. If the cleavage occurs due to trypsin alone, resulting in the loss of 13 N-terminal residues and 23 C-terminal residues, then the lethality was slight less with an $LD_{50}$ 320 ng/kg. As mentioned, the toxin can also be activated by a lambda protease secreted by *Clostridium perfringens*. This cleaves the 10 residues from N-terminus and 29 residues from C-terminus, which results the activity close to maximal with an $LD_{50}$ of 100 ng/kg (Minami et al., 1997). The cleavage also causes a marked shift of pI from 8.02 for the prototoxin to 5.36 in the mature toxin (Worthington and Mulders, 1977). Madin-Darby canine kidney (MDCK) cell line of endothelial origin from the distal convoluted tubule is the most sensitive cell line to epsilon toxin (Payne et al., 1994). In-vitro exposure of MDCK cells with epsilon toxin results cytoskeleton changes and irreversible damage to plasma membrane (Donelli et al., 2003). Cells subsequently swell, develop membrane bleb (Borrmann et al., 2001; Petit et al., 2001). However, there is no evidence of internalization of the toxin (Petit et al., 1997). The binding of epsilon toxin to MDCK cells and rat synaptosomal membrane is associated with formation of stable and SDS resistant high molecular weight complex (Nagahama et al.; 1992; Petit et al.; 1997). The similar large molecular weight complexes has also been observed with other pore forming toxins, such as *Staphylococcus aureus* α-hemolysin (Song and Gouaux, 1998), *C. septicum* α-toxin (Melton et al., 2004), *Pseudomonas aeruginosa* cytotoxin (Ohnishi et al., 1994), and *Aeromonas hydrophila* aerolysin (Wilmsen et al., 1992). Epsilon toxin as many other pore-forming toxins, has been shown to interact specifically with detergent resistant micro-domains (DRMs) of the membrane and form pore (Miyata et al., 2002). This suggests that a putative receptor located in DRMs is responsible for toxin binding and subsequent heptamerization.

In spite of its sequential dissimilarity epsilon toxin has high structural similarity with *Aeromonas hydrophila* aerolysin (Cole et al., 2004) as well as with alpha-toxin of *Clostridium septicum* (Melton-Witt et al. 2006). Because of the structural similarity of Epsilon toxin to aerolysin and other β-pore forming toxins, it seems likely that epsilon toxin shares a related mechanism of pore formation including conformational changes from its secreted water-soluble form. By chemical modification of epsilon toxin, several essential amino acids have been identified for its activity, such as tryptophan, tyrosin and histidine and three or four aspartic or glutamic acid (Sakurai and Nagahama, 1985; Sakurai and Nagahama, 1987a; Sakurai and Nagahama, 1987b; Payne and Osten, 1997; Sakurai and Nagahama, 1987c). Substitution of the two histidine residues either with alanine or serine did not abolished lethal activity of the protein, suggesting that imidazole side-chain does not play a role in activity of the toxin; however, the change with proline results a loss in lethal activity (Oyston et al., 1998). This suggests that structural motif in this region is essential for biological activity, which undergo a conformation change in proline substitution.

There are some crude vaccines existing for the prevention of disease associated with *Clostridium perfringens* type B and D strains. These vaccines are based on formaldehyde-treated cell filtrates or bacterial cells and an equine derived antitoxin. The immunogenicity of these vaccines is variable and the vaccine may not provide complete protection (Percival et al. 1990).

Thus both the existing approaches to combat illness would be of limited significance in case of epsilon (ε) toxin bioterrorism. Due to rapid progression of the disease, treatment is generally not possible, and the emphasis is placed on prevention either by vaccination or by administration of antitoxin to unvaccinated animals in occurrence of enterotoxemia. Therefore an alternative preventive measures are needed that can inhibit the activity of epsilon toxin.

The present invention discloses generation and high level expression of recombinant non-toxic mutant of epsilon toxin of *Clostridium perfringens* and its uses as a recombinant vaccine against *Clostridium perfringens* infection.

OBJECTIVE OF THE PRESENT INVENTION

The main objective of the present invention is to generate a recombinant vaccine against *Clostridium perfringens* and epsilon toxin intoxication.

Another objective of the present invention is to provide the process for generation and high level expression of recombinant non-toxic epsilon toxin protein involving amplifying, cloning, transforming, incubating and purifying the recombinant non-toxic epsilon toxin protein.

STATEMENT OF INVENTION

Accordingly, the present invention relates to the generation and high level expression of recombinant non-toxic mutant of epsilon toxin of *Clostridium perfringens* as a recombinant vaccine against *Clostridium perfringens* infection and a process for producing the recombinant vaccine involving amplifying, cloning, transforming, incubating and purifying the recombinant non-toxic epsilon toxin protein.

BRIEF DESCRIPTION OF DRAWINGS

FIG. 1: shows the mutagenesis strategy of EtxY71G in the prokaryotic expression vector pQE60.

FIG. 7: shows the Cell viability assay. Trypsin-treated rEtx wild type and rEtxY71G from *C. perfringens* was added to the medium overlying MDCK cells in 96-well plates, and the cytotoxicity was assessed by staining cells with the metabolic indicator MTT. Data represent the means and standard deviations for triplicate samples and are expressed relative to the staining of cells not treated with toxin.

Figure 8:
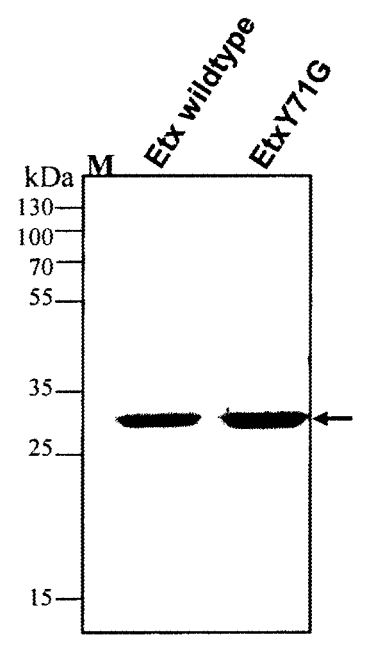

FIG. 8: shows the western blots of Etx wild type and EtxY71G protein against anti-EtxY71G antisera. The specificity and cross reactivity is evident as a single band at the expected size of rEtx.

FIG. 9: shows the antibody titer of collected sera from immunized mice. Groups of 6 mice were immunized with protein preparation at 0, 2 and 4 weeks. Serum samples collected 2 weeks after each immunization were analyzed in triplicates by ELISA.

Figure 2:
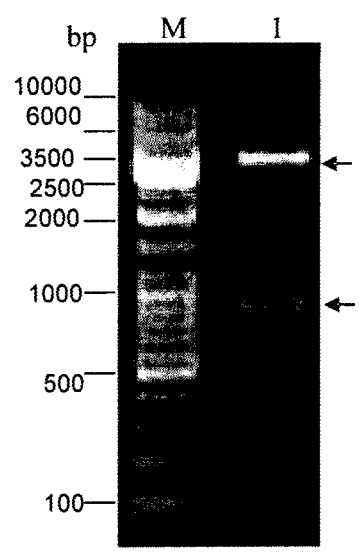
FIG. 2: shows the analysis of mutagenesis product by restriction digestion with NcoI and HindIII. Lane 1 shows linearized pQE60 vector backbone & 846 bp insert fallout indicated by arrow. M indicates DNA molecular wt marker (O'GeneRuler™ DNA Ladder Mix).

Table 1: shows the In-vitro cytotoxicity of rEtx wild type and mutants. Purified wild-type and mutated recombinant epsilon toxin were activated with trypsin. After treating the cells with activated protein, cytotoxicity was determined as the concentration of protein required to kill 50% of MDCK cells.

Table 2: shows the Protection of immunized mice against a lethal challenge by rEtx wild type. Two weeks after the $2^{nd}$ booster, immunized mice (6 mice per group) were challenged i.p. with $150LD_{50}$ of rEtx wild type, and then were observed daily for 14 days.

SUMMARY OF THE INVENTION

The invention is about generation and high level expression of recombinant non-toxic epsilon toxin protein of

*Clostridium perfringens* as a recombinant vaccine against *Clostridium perfringens* infection and epsilon toxin intoxication. This invention also provides a process for producing the vaccine involving amplifying, cloning, transforming, incubating and purifying the recombinant non-toxic epsilon toxin protein.

DETAILED DESCRIPTION OF THE INVENTION

The present invention provides a recombinant non-toxic epsilon toxin protein of *Clostridium perfringens* as a recombinant vaccine against *Clostridium perfringens* infection and ways of generating and expressing the same at high levels. In addition, this invention provides a process for producing the vaccine by various steps involving amplifying, cloning, transforming, incubating and purifying the recombinant non-toxic epsilon toxin protein.

The terms nucleic acids, polynucleotides, genes, or cDNA refer to nucleotides, either ribonucleotides, or deoxyribonucleotides or a combination of both, in a polymeric form of any length.

A nucleic acid encoding an antigenic polypeptide may be any nucleic acid molecule of, for example cDNA, genomic DNA, synthetic DNA or RNA origin or suitable combinations thereof. Administration of the nucleic acid encoding an antigenic polypeptide to a subject can confer an immunoprotective effect to the subject against *C. perfringens*. The nucleic acid may be of any length provided that the immunoprotective activity is maintained by the encoded antigenic polypeptide. The sequence of the nucleic acid encoding an antigenic polypeptide may be based on nucleic acid sequence of this application. A nucleic acid sequence encoding an antigenic polypeptide may be used either singly or in combination with other nucleic acid sequences, encoding antigenic polypeptides or encoding any other desired polypeptide, in the preparation of a vaccine.

The polynucleotides include single stranded DNA or RNA or double stranded DNA. The said terms also include all possible modifications (chemical or substitution with any other naturally occurring or synthetic nucleotide in the cDNA, DNA, mRNA, nucleic acid, polynucleotides, nucleic acid sequences, nucleotide sequence, gene or nucleic acid molecule.

Making of the said nucleic acid sequence in part or full using alternate methods such as recombinant techniques including Polymerase chain reaction using specific primers, or synthetically following a chemical approach is also covered in the scope of this invention.

The DNA sequences as defined in the present invention can be interrupted by intervening sequences such as introns, mobilizable DNA, insertion sequences that disrupt the coding sequences without affecting the translated product. Removal of these intervening sequences restores the coding sequence in the said expressible product.

An Open Reading Frame (ORF) is defined as a nucleotide sequence that can be transcribed into an mRNA and/or translated into a polypeptide when placed under appropriate regulatory sequences. An ORF can include, but is not limited to RNA, DNA, mRNA, cDNA, recombinant nucleotide sequences, synthetically made polynucleotide sequences or genomic DNA. The polynucleotides sequence as given can be translated into different frames and all the translated products fall within the scope of the present invention.

A suitable vector may be any vector (for example, a plasmid or virus) which can incorporate a nucleic acid sequence encoding an antigenic polypeptide and any desired control sequences and can bring about the expression of the nucleic acid sequence. The choice of the vector will typically depend on the compatibility of the vector with a host cell into which the vector is to be introduced.

In certain examples, the vector may exist as an extrachromosomal entity, with replication being independent of chromosomal replication, for example, a plasmid, an extrachromosomal element, a minichromosome, or an artificial chromosome.

In other examples, the vector may be one which, when introduced into the host cell, is integrated into the genome and replicated together with the chromosome(s) into which it has been integrated. Still other examples of vectors and techniques for manipulating vectors will be known and apparent to the skilled person.

The kit according to this invention comprises compositions or vaccines in relation to the method of immunization proposed. The kit according to the invention therefore comprises a container containing various containers containing the compositions or vaccines and advantageously, and optionally, an explanatory brochure including useful information for administration of the said compositions or vaccines.

The recombinant epsilon toxin together with the buffer conditions described or known till date and co-solvents and adjuvants can be used to raise antiserum against the epsilon toxin that can be a component of a diagnostic kit to detect *Clostridium perfringens* infection.

Heat treatment of the protein EtxY71G (SEQ ID NO:3) did not affect its immunogenic and protective potential against the epsilon toxin of *C. petfringens*.

When introducing elements disclosed herein, the articles "a", "an", "the", and "said" are intended to mean that there are one or more of the elements unless the context dictates otherwise. For example, the term "a compound" and "at least one compound" may include a plurality of compounds, including mixtures thereof.

The terms "comprising", "having", "including" are intended to be open-ended and mean that there may be additional elements other than the listed elements. As is understood by the skilled person, administration of a vaccine can be done in a variety of manners. For example, administration may be done intramuscularly, subcutaneously, intravenously, intranasally, intradermaly, intrabursally, in ovo, ocularly, orally, intra-tracheally or intra-bronchially, as well as combinations of such modalities. The dose of the vaccine may vary with the size of the intended vaccination subject.

This invention also provides the immunogenic potential of recombinant non-toxic epsilon toxin protein and its use as a vaccine for the treatment of *Clostridium perfringens* infection generally in mammals and particularly in mice.

It is an important embodiment of the present invention to use of the non toxic EtxY71G as a protein vaccine.

In a preferred embodiment of the present invention the gene encoding the non toxic epsilon toxin protein is cloned in the bacterial expression vector pQE60 and the recombinant protein is over expressed.

In another embodiment of the present invention the expressed recombinant protein is present in a soluble form in the cell lysate.

In yet another embodiment of the present invention the recombinant protein is purified by DEAE sepharose anion exchange chromatography with high yield of homogeneous recombinant protein.

In still another embodiment of the present invention the purified recombinant EtxY71G is completely non-toxic to MDCK cells and mice.

In another embodiment of the present invention the purified recombinant protein is highly immunogenic in mice. The antisera generated exhibit high antibody titers and possess neutralizing antibodies as determined by cell viability assay of MDCK cells.

It is yet another embodiment of the present invention the use as a vaccine is confirmed by challenging the immunized animals with Epsilon toxin wild type.

In still another embodiment of this invention, the recombinant vaccine produces high antibody titers of $10^{-6}$ It is another embodiment of the present invention a process for producing the vaccine by:
  a. substituting amino acid in epsilon toxin gene by site directed mutagenesis PCR with complimentary primers, forward primer SEQ.ID NO 1 and reverse primer SEQ.ID.NO 2,
  b. amplifying the gene of step (a) in PCR,
  c. digesting the amplified genes obtained from step (b) with restriction enzymes,
  d. generating a mutation in epsilon toxin gene,
  e. over expressing the soluble form of recombinant EtxY71G from the resultant positive clone pQE60EtxY71G,
  f. purifying the recombinant non-toxic epsilon toxin protein in a single step, and
  g. checking for nontoxicity.

It is still another embodiment of the present invention the restriction enzymes are NcoI and HindIII.

It is further embodiment of the present invention to carry out the cloning in *E. coli* DH5α strain.

In yet another embodiment of the present invention the expression analysis is carried in M15 strain.

In yet another embodiment of this invention upto 100 mg/L of highly immunogenic and homogenous recombinant EtxY71G protein of 31 kDa was produced by the process.

It is another embodiment to have a kit comprising,
  a. the recombinant non-toxic epsilon toxin protein,
  b. buffer,
  c. co-solvents,
  d. adjuvant, and
  e. an explanatory brochure.

Chemicals Used

All the chemicals were purchased from Sigma-Aldrich USA unless otherwise mentioned. Media for bacterial culture were purchased from Difco laboratory, USA. DNA ladders and protein molecular weight markers were obtained from MBI Fermentas. Quick change site directed muatagenesis kit was purchased from Stratagene, Germany. DEAE sepharose for anion exchange chromatography was obtained from Amersham Pharmacia Biotech, UK. Oligonucleotides for PCR amplification were synthesized from Sigma-Aldrich USA. Eagle minimum essential medium (MEM), antibiotic-antimycotic mix and Trypsin-EDTA are obtained from Gibco BRL, USA. Fetal calf serum was from Biological Industries, Israel.

Bacterial Culture

*E. coli. DH*5α strain (Novagen, USA) was used for cloning purposes and M15 strain (Qiagen, Germany) was used for expression analysis. All the bacterial cultures were grown in Luria Bertani (LB) medium (Bacto-tryptone 1%, Yeast extract 0.5% and NaCl 1%, pH 7.0) at 37° C. with 220 rpm rotary shaking with 100 μg/ml ampicillin selection. The medium was sterilized by autoclaving at 15 lbs/square inch for 20 min. LB agar was prepared by adding 1.5% agar to LB medium prior to autoclaving.

Technique Used

PCR site-directed mutagenesis, technique was used and the result was accomplished using polymerase chain reaction with oligonucleotide "primers" that contain the desired mutation. As the primers are the ends of newly-synthesized strands, by engineering a mis-match during the first cycle in binding the template DNA strand, a mutation can be introduced. Because PCR employs exponential growth, after a sufficient number of cycles the mutated fragment will be amplified sufficiently to separate from the original, unmutated plasmid by a technique such as gel electrophoresis, and reinstalled in the original context using standard recombinant molecular biology techniques.

For plasmid manipulations, this technique has largely been supplanted by a PCR-like technique where a pair of complementary mutagenic primers is used to amplify the entire plasmid. This generates a nicked, circular DNA which can undergo repair by endogenous bacterial machinery. However, this process does not amplify the DNA exponentially, but linearly. Yields are complicated by the fact that the product DNA must undergo the nick repair and is not supercoiled, resulting in reduced efficiency of bacterial transformation. Finally, the product DNA is of the same size as the plasmid. Therefore, the template DNA must be eliminated by enzymatic digestion with a restriction enzyme specific for methylated DNA. The template, which for this technique should be biosynthesized will be digested, but the mutated plasmid is preserved because it was generated in vitro and is therefore unmethylated.

Evaluation of Recombinant Non-Toxic EtxY71G of *Clostridium perfringens* as a Vaccine:

In order to use epsilon toxin for immunological and biological studies, it is vital to have sufficient amount of protein in pure and properly folded form. For this purpose mutation has been generated in the prokaryotic expression vector pQE60 under the control of T5 promoter. Since T5 RNA polymerase is not endogenous to bacteria, *E. coli.* M15 (pREP4) strain had been engineered to carry the gene encoding for this RNA polymerase. Successful and efficient expression of the recombinant EtxY71G was obtained using this expression system. Purified rEtxY71G was evaluated for its immunogenic and vaccine potential. Details of the same are described below in the form of following illustrative examples.

The following non limiting examples are provided to illustrate the embodiment of the present invention.

EXAMPLE 1

Generation of Mutation in Recombinant Epsilon Toxin of *Clostridium perfringens*

Figure 1:
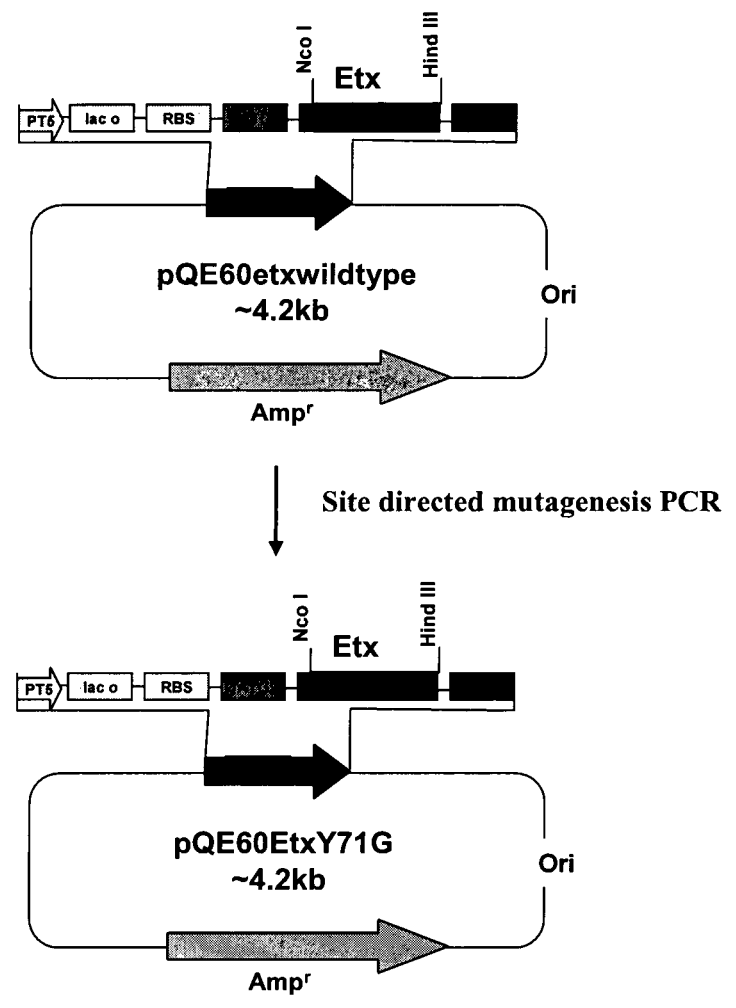

Amino acid substitution mutation was made in epsilon toxin gene by PCR amplification using complementary primers by site-directed mutagenesis kit as per the manufacturer's instructions. For this purpose, a forward and reverse primers represented by SEQ.ID.No:1, (5'-CCATCAATGAATTATCTTGAAGATGTT<u>GGT</u>GTTGGAAAAGCTCTC-3') and SEQ.ID.NO:2, (5'-GAGAGCTTTTCCAAC<u>ACC</u>AACATCTTCAAGATAATTCATTGATGG-3') respectively, were synthesized. Earlier cloned epsilon toxin gene in pQE60 vector at NcoI and HindIII restriction sites was used as template for mutagenesis PCR (FIG. 1). The PCR was carried out in Perkin Elmer thermal cycler. The transformants were analyzed by restriction digestion with NcoI and HindIII (FIG. 2). Plasmid DNA was isolated from the transformants by MDI mini prep kit as per manufacturer's instructions and further sequenced by automated DNA sequencer at University of Delhi, south campus, New Delhi to confirm the incorporation of the intended mutation. The resultant positive clone pQE60EtxY71G was further carried out for expression analysis.

EXAMPLE 2

Analysis of Expression of Recombinant EtxY71G

Figure 3:
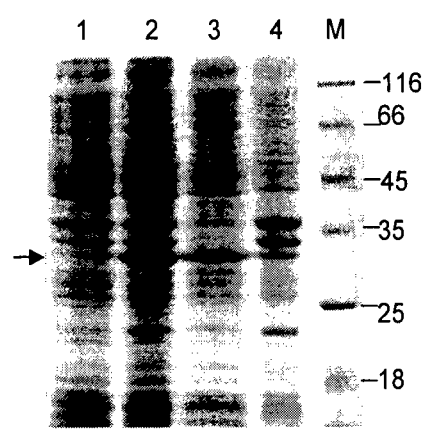
FIG. 3: shows the expression and localization of recombinant EtxY71G in *E. coli* M15 cells harboring plasmid pQE60EtxY71G under the control of T5 promoter. Lane 1 shows uninduced whole cell lysate, Lane 2 shows induced whole cell lysate, Lane 3 shows soluble fraction of induced culture and Lane 4 shows insoluble fraction of induced culture. M indicates fermentas unstained protein marker and arrow indicates expressed recombinant EtxY71G in 12% SDS PAGE.

To check the expression of recombinant EtxY71G, pQE60EtxY71G construct was transformed in *E. coli* M15 cells. A single colony from the transformed plate was inoculated in 10 ml of autoclaved LB media with 100 µg/ml ampicillin antibiotic and allowed to grow for O/N at 37° C. with constant shaking at 220 rpm. The cells were subcultured (1%) in fresh LB with 100 m/ml ampicillin and induced with 1 mM IPTG (isopropyl-β-D-thiogalactopyranoside) when $A_{600}$ reached 0.6. Cells were allowed to grow in the similar condition for 4-6 hr post induction and then harvested. Uninduced and induced total cell lysates were prepared by resuspending the cells pellets in 1× Laemmli sample buffer and boiled for 10 min. Total cell extracts were checked on 12% SDS PAGE (Laemmli 1970; Nature 15, 227:680-685) for expression of EtxY71G. The production of the recombinant protein was evident by a protein band of expected size ~31 kDa. Uninduced total cell extract did not show any band at this position indicating a stringent control over the expression of the protein (FIG. 3; lane 1 & 2). To check the localization of the expressed product, induced cells were fractionated into soluble and insoluble fractions by sonication at 70% amplitude and 0.5 cycles for 5 minutes (Hielscher UP100H, Germany). The sonicated product was centrifuged at 4° C. and 12000 rpm and the supernatant thus obtained was considered as soluble fraction and the pellet was considered as insoluble fraction. The soluble and insoluble fraction analysis on 12% SDS-PAGE indicated that the expressed product was mostly present in soluble fraction (FIG. 3; lane 3 & 4).

EXAMPLE 3

Purification of Recombinant EtxY71G

Figure 4:
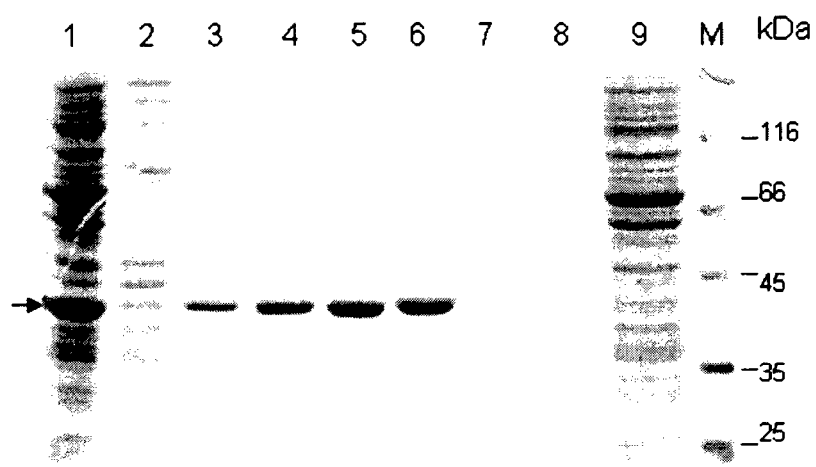
FIG. 4: shows the purification of recombinant EtxY71G using DEAE sepharose anion exchange chromatography. Lane 1 shows soluble fraction of induced culture of *E. coli* M15 cells harboring plasmid pQE60EtxY71G, Lane 2-7 show different fractions collected during wash by 10 mM Tris-HCl pH 7.5, Lane8-9 show 2M NaCl wash fractions. M indicates Fermentas unstained protein molecular weight marker and arrow indicates expressed recombinant EtxY71G in 12% SDS PAGE.

The recombinant protein EtxY71G was purified using DEAE sepharose anion exchange chromatography from the soluble fraction. *E. coli* M15 cells harboring plasmid pQE60EtxY71G were induced with 1 mM IPTG at 0.6 $A_{600}$ and allowed to grow for 4 hr at 37° C. and 220 rpm. The induced cells were harvested and fractionated into soluble and insoluble fractions by sonication in 10 mM Tris-Cl, pH 7.5 buffer. The sonicated product was centrifuged at 4° C. and 12000 rpm, supernatant fraction was considered as soluble fraction. It has been observed that above pH 8.0, recombinant EtxY71G binds to the DEAE sepharose resin and pH≤8.0, all other protein of soluble fraction got binds to the resin and EtxY71G comes in the wash out fractions. So for the easiest way, soluble fraction was loaded onto a DEAE Sepharose anion exchange column (equal culture volume) pre-equilibrated with 10 mM Tris-Cl, pH 7.5. Then the column was washed with 10 mM Tris-Cl, pH 7.5 and the purified recombinant EtxY71G fractions were analyzed on 12% SDS PAGE and found the purification was near-homogeneity (FIG. 4). The purified fractions were polled and concentrated by Amicon Ultra centrifugal filter device (Millipore, USA) with 10 kDa and stored at −20° C. till further usage.

EXAMPLE 4

Figure 5:
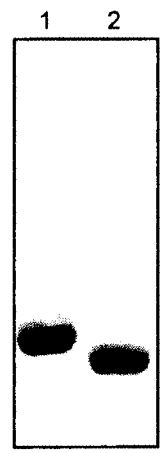
FIG. 5: shows the activation of rEtxY71G protein by trypsin treatment at room temperature. Lane 1 shows untrypsinized protein and lane 2 shows trypsin activated protein.
Figure 6:
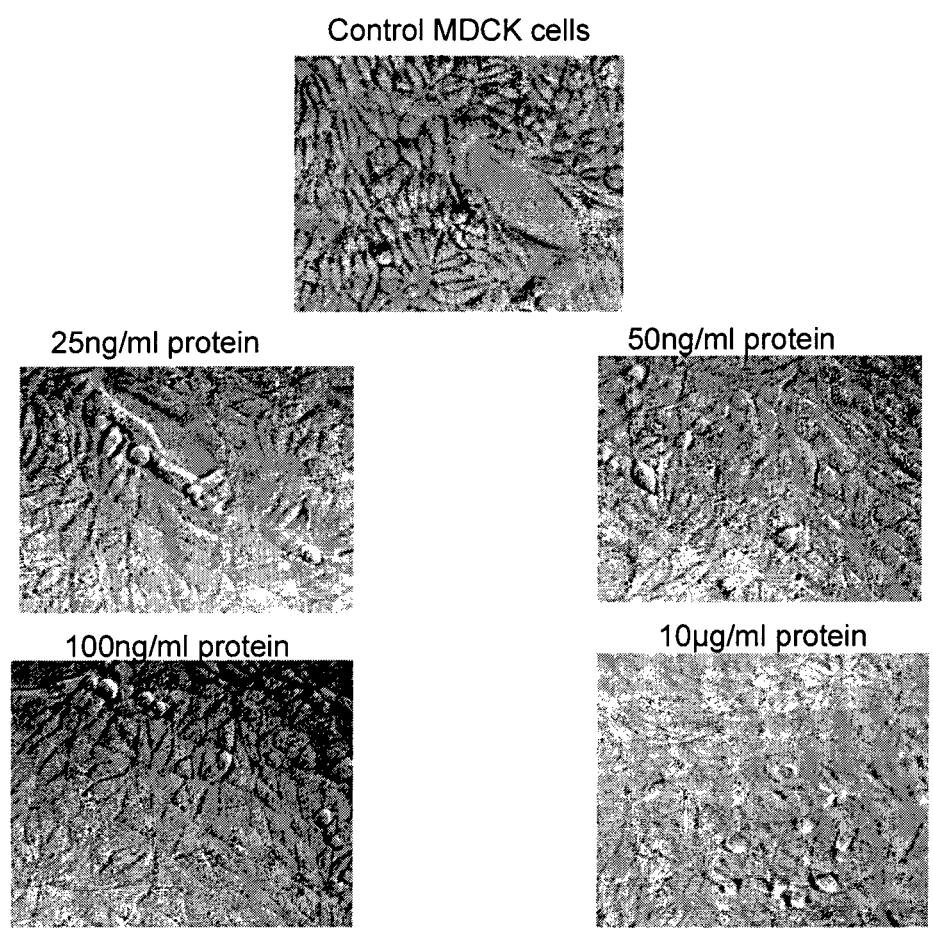
FIG. 6: shows the effect of rEtxY71G on morphology of MDCK cells. MDCK cells were incubated with different concentration of rEtxY71G at 37° C. in 5% $CO_2$. The cells were monitored after 2 hr of incubation under phase contrast microscope at a magnification of 10×.

(a) In vitro Cytotoxicity of Recombinant EtxY71G Protein:

This example discloses the evaluation of recombinant EtxY71G as a non-toxic protein to MDCK cells and experimental mice BALB/c. To check the activity of recombinant EtxY71G, first of all protein was incubated with trypsin (1/200 w/w) at 37° C. or room temperature for 1 h and analysed on SDS-PAGE for the removal of 23 residues from C-terminus (FIG. 5). The activity of recombinant EtxY71G was checked by in vitro toxicity assays on MDCK cells. MDCK cells were cultured in 24 well plate at a density of 4–5×10$^5$ cells/ml (1 ml/well) with Eagle's minimum essential media containing 10% Fetal calf serum and antibiotic-antimycotic mix. After maintaining the cells in 5% $CO_2$ at 37° C. for 16 h, different concentrations of recombinant EtxY71G was added to the cells with growth medium and maintained the cells in 5% $CO_2$ at 37° C. for 2 h. Cells were visualized under phase contrast microscope and found no any remarkable change in morphology corresponding to untreated cells (FIG. 6), at the same time recombinant Etx wild type showed complete cell death with much lower concentration.

(b) MTT Cell Viability Assay:

The assay is based on the capacity of living cells to reduce yellow tetrazolium MTT (3-(4,5-dimethylthiazolyl-2)-2,5-diphenyltetrazolium bromide) to intracellular purple formazan which can be dissolved in DMSO and quantified by spectrophotometry.

Figure 7:
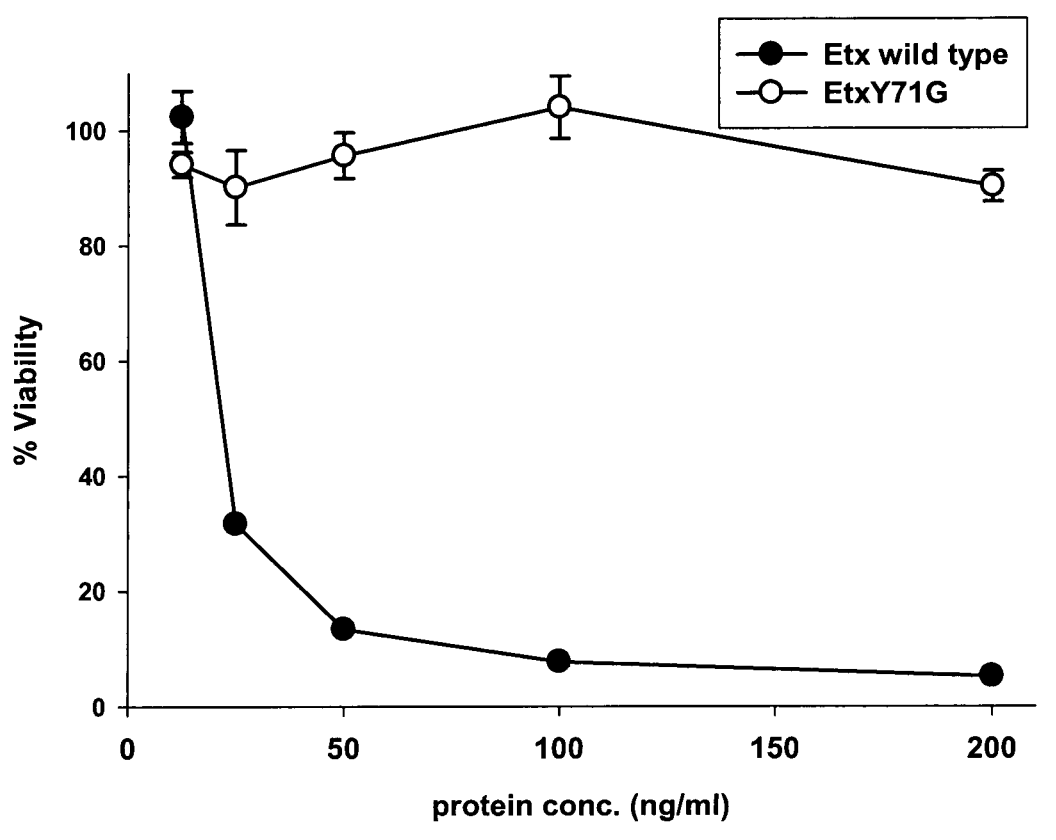

MDCK cells were grown to 80% confluence in 96 well microtiter plates with Eagle's minimum essential media containing 10% fetal calf serum and antibiotic-antimycotic mix. After maintaining the cells in 5% $CO_2$ at 37° C., different concentration of trypsin activated recombinant EtxY71G were added to cells and incubated for 2 hr at 37° C. in 5% $CO_2$. As per the positive control, different concentration of trypsin activated recombinant Etx wild type was added to cells in different wells. After maintaining the cells in 5% $CO_2$ at 37° C. for 2 h, 0.25 mg/ml MTT (Sigma-Aldrich) was added with complete MEM to the cells and maintained for 2 h at 37° C. After removing solutions from well, cells were then lysed by 100 µl DMSO. Dissolved formazan was measured at 540 nm in a 96 well microtiter plate reader. The experiment was done three times for each treatment, and means and standard deviation were obtained and compared statistically. There was no toxicity in case of recombinant EtxY71G (FIG. 7). This was further validated in case of experimental mice BALB/c and found 100% survival.

EXAMPLE 5

Immunization of Test Animal BALB/c Mice and Immunoblot Analysis to Determine the Specificity of Antisera:

This example discloses the evaluation of recombinant EtxY71G (rEtxY71G) as a vaccine candidate against *Clostridium perfringens* infection and epsilon toxin intoxication. To test the potential of recombinant EtxY71G as a vaccine candidate, the immunogenic potential of the same is evaluated.

BALB/c mice were immunized on day 0 with 10 µg pure protein emulsified in complete Freund's adjuvant. The animals were given two booster doses at intervals of two weeks with the same dose of antigen emulsified in incomplete Freund's adjuvant. Blood was collected from the retro orbital plexus two week after every immunization. Serum was prepared from the whole blood and analyzed by immunoblot for the specificity of antibody. The proteins were separated by SDS-PAGE and electrotransferred onto nitrocellulose (NC)

membrane in transfer buffer (25 mM Tris-Hcl pH 8.3, 192 mM glycine, 1% SDS and 15% methanol) using Bio-Rad transblot apparatus at 4° C. and 100V for 2 h. After the transfer, non specific sites on NC membrane were blocked by 3% fat free milk in PBST (1×PBS and 0.05% Tween-20) for 1 h at room temp with shaking. The membrane was then incubated with dilution of primary antibody (collected sera) followed by dilution of HRP conjugated anti-mouse IgG (secondary antibody) with 3% fat free milk in PBST for 2 h at room temp. The blot was washed thoroughly with PBST between successive incubations Immunoreactive protein band was visualized by diamino-benzidine (0.5 mg/ml in PBS) and 1 µl/ml $H_2O_2$ and the reaction was terminated by milli Q water. The anti-rEtxY71G antisera were able to detect recombinant EtxY71G as well as Etx wild type (FIG. 8). This suggests the presence of highly specific anti-rEtx antibodies with cross reactivity to wild type.

EXAMPLE 6

Antibody Titer Determination of Anti-Retxy71G Antisera Raised in Mice using Enzyme Linked Immunosorbent Assay (ELISA)

Figure 9:
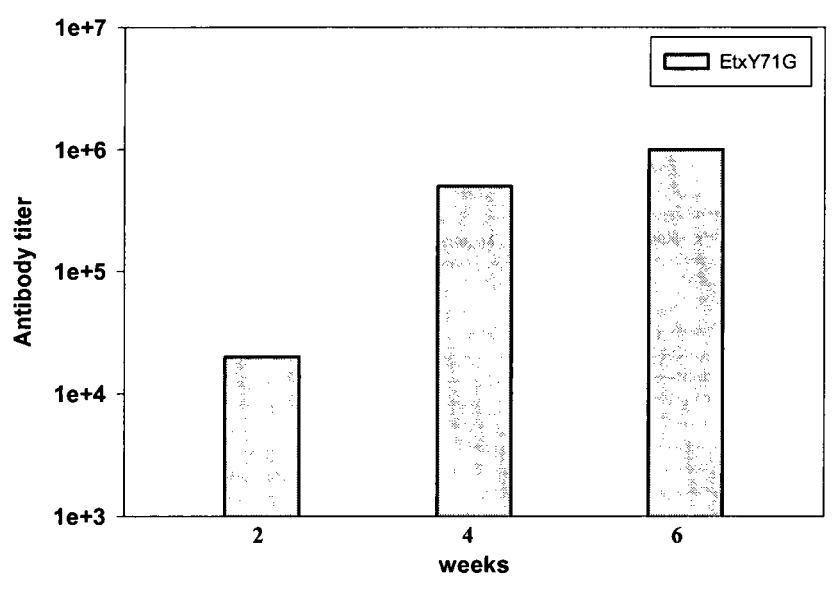

Antigen specific ELISA was performed to determine the titer of antisera collected after every immunization. The end-point titers were determined as the maximum serum dilution which gave an absorbance above the background level. Immune serum collected from negative control mice, administered with CFA+PBS only. Purified recombinant Etx (250 ng/well) was coated with coating buffer (0.2 M carbonate-bicarbonate buffer, pH 9.2) in 96 well microtiter plates and incubated at 37° C. for 1 h. Non specific sites were blocked by 5% non-fat milk in PBST. Different dilutions of collected sera in PBS with 2% BSA (100 µl/well) were added to the wells and incubated for 2 h at 37° C. HRP conjugated anti-mouse IgG 1:10000 in PBS with 2% BSA (100 µl/well) were added and incubated at 37° C. for 1 h. Wells were thoroughly washed between successive incubations with PBST (0.05% Tween-20 in 1×PBS). Color was developed in 0.5 mg/ml orthophenylene-diamine (OPD) in citrate phosphate buffer (pH 5.5) along with hydrogen peroxide (1 µl/ml). The reaction was terminated by the addition of 50 µl of 2N $H_2SO_4$ and quantified by measuring the absorbance at 490 nm using BioTek microplate reader. There was remarkably high antibody response with titers $10^6$ in mice for anti-rEtxY71G (FIG. 9), proving that the EtxY71G has better immunogenic potential.

EXAMPLE 7

Analysis of Type of Immune Response

Protective immunity to enteric pathogen is partially dependent on the activation of cellular defense mechanism by T cells. Intracellular bacteria and parasites stimulate T-helper cells, which consists of distinct subsets Th1 and Th2 based on their cytokine secretion profile (Mosmann and Coffman 1989). Th1 cells secrete 11-2, interferon gamma (IFN-γ), tumor necrosis factor alpha and beta (TNFα and β) and are associated with cell mediated immunity and IgG classes switch to IgG2a. Th2 cells secrete IL-4, IL-5, and IL-10 and promoter humoral response by activating B cells and IgG classes switch to IgG1.

Antigen-specific IgG subclasses (IgG1, IgG2a and IgG2b) levels in the sera were determined by direct ELISA. Wells of microtiter plate were coated with 100 µl of rEtx protein (10 µg/ml) in coating buffer (0.2 M carbonate-bicarbonate buffer, pH 9.2) and incubated for 1 h at 37° C. or O/N at 4° C. Non specific sites were blocked by 5% non-fat milk in PBST.

Figure 10:
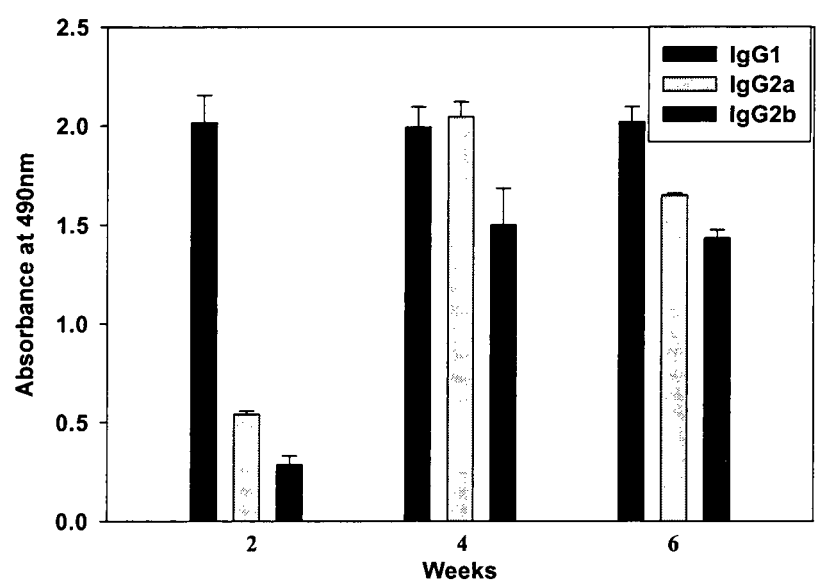
FIG. 10: shows the IgG isotype profile of antigen specific serum antibodies of mice immunized through intra-peritoneal route. Experiments were done in triplicates for sera collected between 2-6 weeks and data are represented as mean absorbance±S.D.

Dilution of sera in PBS with 2% BSA (100 µl/well) were added and incubated for 2 h at 37° C. Then after biotin conjugated different isotypes of IgG (1:1000) in PBS with 2% BSA (100 µl/well) were added and incubated at 37° C. for 2 h followed by Sav-HRP (1:1000) in PBS with 2% BSA (100 µl/well) for 1 h. Wells were thoroughly washed between successive incubations with PBST (0.05% Tween-20 in 1×PBS). Color was developed in 0.5 mg/ml ortho-phenylenediamine (OPD) in citrate phosphate buffer (pH 5.5) along with hydrogen peroxide (1 µl/ml). The reaction was terminated by the addition of 50 µl of 2N $H_2SO_4$ and quantified by measuring the absorbance at 490 nm. There was a dominating IgG1 response after primary immunization (2 week sera), which depict predominant Th2 response (humoral). After $1^{st}$ booster there was mixed IgG1/IgG2a/IgG2b responses, which depict mixed Th1-Th2 response (FIG. 10). A mixed immune response indicates that immunization with the recombinant EtxY71G results in activation of both the arm of immune system (humoral and cellular), thus providing it to be a good vaccine candidate.

EXAMPLE 8

Protective Efficacy of Recombinant EtxY71G Immunization

In order to assess the protective potential of immunization with the recombinant EtxY71G against epsilon toxin intoxication, both in vitro neutralization and in vivo challenge studies were carried out.

(i) In Vitro Studies

Figure 11:
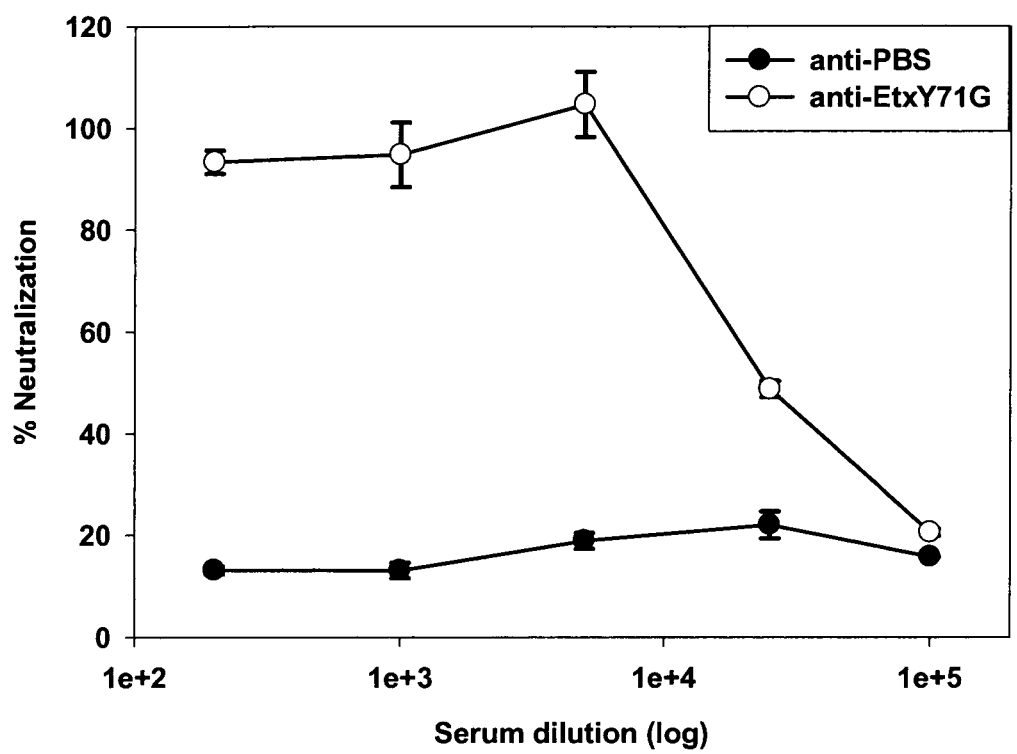
FIG. 11: shows the In vitro neutralization of epsilon toxin. Epsilon toxin (25 ng per ml) was incubated for 1 h at 37° C. with different dilutions of sera. The toxin-antibody mixtures then were added to 80% confluent MDCK cells monolayer and incubated at 37° C. for 2 h. Cytotoxicity was assessed by staining cells with the metabolic indicator MTT. Data represent the means and standard deviations for triplicate samples and are expressed relative to the staining of cells not treated with toxin.

For in vitro studies epsilon toxin neutralization test was performed on the MDCK cells with collected sera of rEtxY71G immunized mice and control mice. Different serial dilutions of sera were mixed with equal volume of trypsin activated epsilon toxin with complete MEM and preincubated at 37° C. for 1 h b. Then after, cells were treated with epsilon toxin and anti-EtxY71G antibody mixture. After the incubation of 2 h at 37° C. 0.25 mg/ml MTT (Sigma-Aldrich) was added with complete MEM and maintained for 1 hr at 37° C. After removing solutions from wells 100 µl DMSO was added to the wells and dissolved formazan was measured at 540 nm in a 96 well microtiter plate reader (Bio-Tek). There was a significant reduction in toxicity of recombinant Etx wild type with anti-EtxY71G antibody (FIG. 11). The results obtained are tabulated in Table 1 as follows.

TABLE 1

| Protein | Expression | | Trypsin activation of purified protein | Mean $CT_{50}$ (ng/ml) |
|---|---|---|---|---|
| | Soluble | Insoluble | | |
| rEtx wild type | Yes | No | Yes | 15 |
| rEtxC94A | Yes | No | Yes | 10 |
| rEtxC94R | Yes | No | Yes | 5 |
| rEtxC94W | Yes | No | Yes | 17 |
| rEtxY71G | Yes | No | Yes | Non toxic |
| rEtxY169G | Yes | No | Yes | 9 |
| rEtxY254G | Yes | No | Yes | 10 |
| rEtxW190P | Yes | Yes | degradation | — |
| rEtxW190A | Yes | Yes | Yes | 74 |
| rEtxF92G | Yes | No | Yes | 116 |
| rEtxY231F | Yes | No | Yes | 23 |
| rEtxY231P | No | Yes | — | — |
| rEtxY231K | No | Yes | — | — |
| rEtxY231A | Yes | Yes | degradation | — |
| rEtxY231L | Yes | No | Yes | 55 |

Table 1, depicts the In-vitro cytotoxicity of rEtx wild type and mutants. The purified wild-type and mutated recombinant epsilon toxin were activated with trypsin and the cytotoxicity was determined as the concentration of protein required to kill 50% of MDCK cells.

(ii) In Vivo Studies

For in vivo challenge studies rEtxY71G immunized mice and control mice were given 150 $LD_{50}$ doses of epsilon toxin after 2 weeks of $2^{nd}$ booster immunization. The observed results are tabulated in Table 2. It was observed that 100% control mice died within 2 h of challenge whereas there were no death in rEtxY71G immunized mice (100% survival) till 2 weeks.

| Mice immunized with | Number of surviving mice/total number of mice 150$LD_{50}$ challenge dose |
|---|---|
| rEtxY71G | 6/6 |
| PBS | 0/6 |

Table 2: shows the Protection of immunized mice against a lethal challenge by rEtx wild type. Two weeks after the $2^{nd}$ booster, immunized mice (6 mice per group) were challenged i.p. with 150$LD_{50}$ of rEtx wild type, and then were observed daily for 14 days.

Thus in this study substitution mutation Y71G was executed in recombinant Etx and the recombinant EtxY71G protein was over-expressed in soluble form. Expressed protein was purified near homogeneity by DEAE sepharose anion exchange chromatography with high yield.

Potential of rEtxY71G as a vaccine candidate was evaluated and found to be highly specific and immunogenic. The present invention is the first report for high level expression of non toxic rEtxY71G mutant protein of *Clostridium perfringens*. Upto 100 mg/L of highly immunogenic and homogeneous recombinant EtxY71G protein of 31 kDa was produced. Further, the immunization with rEtxY71G gave very high titer and conferred protection against epsilon toxin intoxication.

EXAMPLE 9

Kit(s)

The non toxic recombinant epsilon toxin together with the buffer conditions with co-solvents and adjuvants can be used to raise antiserum against the epsilon toxin. So, this invention can be made either into a diagnostic kit or a vaccine kit, comprising compositions or vaccines in relation to the method of immunization proposed. Adjuvants include, for example, an oil emulsion (e.g., complete or incomplete Freund's adjuvant).

Suitable buffers include, but are not limited to, phosphate buffered saline $Ca^{++}/Mg^{++}$ free (PBS), normal saline (150 mM NaCl in water), and Tris buffer.

Solvents are selected from Chloroform, Ethanol, methanol, etc.

The kit therefore comprises a package containing various containers with the compositions or vaccines and advantageously, and optionally, an explanatory brochure including useful information for administration of the said compositions or vaccines. Heat treatment of the non toxic recombinant epsilon toxin protein did not affect its immunogenic and protective potential against the epsilon toxin of *C. perfringens* no special requirement is needed for storing the kit.

---

The invention claimed is:

1. A recombinant vaccine against *Clostridium perfringens* infection and epsilon toxin intoxication, comprising a recombinant non-toxic epsilon protein of *Clostridium perfringens* wherein said epsilon protein is EtxY71G wherein the recombinant protein has the amino acid sequence set forth in SEQ ID NO:3.

2. The recombinant vaccine as claimed in claim 1, wherein said vaccine is used for the treatment of *Clostridium perfringens* infection and epsilon toxin intoxication in a mammal.

3. The recombinant vaccine as claimed in claim 2, wherein said mammal is a mouse.

4. The recombinant vaccine as claimed in claim 1, wherein the recombinant protein is present in soluble form.

5. The recombinant vaccine as claimed in claim 1, wherein said vaccine produces high antibody titers of $10^6$.

6. The recombinant vaccine as claimed in claim 1, wherein said protein is completely non-toxic to MDCK cells and mice.

7. A process for producing the recombinant vaccine of claim 1 comprising the steps of:
   (a) substituting an amino acid in the epsilon toxin gene cloned in expression vector pQE60 by site directed mutagenesis polymerase chain reaction (PCR) with complimentary primers, forward primer SEQ ID NO: 1 and reverse primer SEQ ID NO:2 to result in expression vector pQE60EtxY71G,
   (b) digesting the mutagenized epsilon toxin gene obtained from step (a) with restriction enzymes NcoI and HindIII to analyze the mutagenized epsilon toxin gene product,
   (c) analyzing the expression of gene rETxY71G, by over expressing the soluble form of recombinant EtxY71G from resultant positive clone pQE60EtxY71G,
   (d) purifying the recombinant non-toxic epsilon toxin protein in a single step, and
   (e) checking for nontoxicity.

8. The process as claimed in claim 7, wherein said pQE60EtxY71G is cloned in *E. coli*. DH5α strain.

9. The process as claimed in claim 7, wherein said expression analysis is carried in M15 strain.

10. The process as claimed in claim 7, wherein said purification of the recombinant non-toxic epsilon toxin protein is carried by DEAE sepharose anion exchange chromatography with high yield of homogeneous recombinant protein.

11. The process as claimed in claim 7, wherein said process produces up to 100 mg/L of highly immunogenic and homogenous recombinant EtxY71G protein of 31 kDa was produced.

12. A kit comprising,
   a. the recombinant non-toxic epsilon toxin protein of claim 1,
   b. buffer,
   c. co-solvents,
   d. adjuvant, and
   e. an explanatory brochure.

* * * * *